(12) United States Patent
Khan

(10) Patent No.: US 11,744,795 B2
(45) Date of Patent: *Sep. 5, 2023

(54) METHOD FOR CONTROLLING DENTAL CARIES AND TREATING TEETH SENSITIVITY

(71) Applicant: Imam Abdulrahman Bin Faisal University, Dammam (SA)

(72) Inventor: Abdul Samad Khan, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/705,904

(22) Filed: Mar. 28, 2022

(65) Prior Publication Data

US 2022/0211609 A1 Jul. 7, 2022

Related U.S. Application Data

(63) Continuation of application No. 16/252,039, filed on Jan. 18, 2019, now Pat. No. 11,318,087.

(51) Int. Cl.

| | | |
|---|---|---|
| *A61Q 11/00* | (2006.01) | |
| *A61K 8/34* | (2006.01) | |
| *A61K 8/9789* | (2017.01) | |
| *A61K 8/27* | (2006.01) | |
| *A61K 8/29* | (2006.01) | |
| *A61K 8/25* | (2006.01) | |
| *A61K 8/46* | (2006.01) | |
| *A61K 8/368* | (2006.01) | |
| *A61K 8/73* | (2006.01) | |

(52) U.S. Cl.
CPC .............. *A61K 8/9789* (2017.08); *A61K 8/25* (2013.01); *A61K 8/27* (2013.01); *A61K 8/29* (2013.01); *A61K 8/345* (2013.01); *A61K 8/368* (2013.01); *A61K 8/463* (2013.01); *A61K 8/731* (2013.01); *A61Q 11/00* (2013.01); *A61K 2800/28* (2013.01); *A61K 2800/48* (2013.01); *A61K 2800/524* (2013.01)

(58) Field of Classification Search
None
See application file for complete search history.

(56) References Cited

U.S. PATENT DOCUMENTS

| | | | |
|---|---|---|---|
| 5,256,402 A | 10/1993 | Prencipe | |
| 6,086,374 A | 7/2000 | Litkowski | |
| 6,143,281 A | 11/2000 | Alexander | |
| 6,162,447 A | 12/2000 | Fankhauser et al. | |
| 8,652,495 B2 | 2/2014 | Porter | |
| 2007/0258916 A1 | 11/2007 | Ferracane et al. | |
| 2009/0324516 A1* | 12/2009 | Muscle | C03C 4/0007 424/52 |
| 2013/0287708 A1 | 10/2013 | Silberstein et al. | |
| 2014/0308219 A1 | 10/2014 | Ibrahim | |

FOREIGN PATENT DOCUMENTS

| | | |
|---|---|---|
| CN | 103445977 B | 5/2016 |
| JP | 60-54312 | 3/1985 |
| JP | 8-175941 | 7/1996 |
| KR | 101992927 B1 | 6/2019 |

OTHER PUBLICATIONS

Dr. Young et al, 2016. (https://www.eqdental.com/one-minute-or-two-how-long-should-you-brush/#:~:text=Most%20dentists%20agree%20that%20two,is%20especially%20true%20for%20children.) (Year: 2016).*

Sprinjene ; Sprinjene Natural Sensitivity Relief Cavity Protection Toothpaste with Black Seed Oil & Zinc—3.5 oz ; https://www.vitacost.com/sprinjene-natural-sensitivity-relief-cavity-protection-tooth paste-with-black-seed-oil-zinc.

Taha, et al. ; The effect of bioactive glasses on enamel remineralization: A systematic review ; Journal of Dentistry, vol. 67 ; pp. 9-17 ; Dec. 2017 ; 2 Pages ; Abstract Only.

Luiza Pereira Dias da Cruz, et al. ; Dentine Tubule Occlusion by Novel Bioactive Glass-Based Toothpastes ; International Journal of Dentistry ; vol. 2018 ; Apr. 4, 2018 ; 11 Pages.

* cited by examiner

*Primary Examiner* — Celeste A Roney
(74) *Attorney, Agent, or Firm* — Oblon, McClelland, Maier & Neustadt, L.L.P.

(57) ABSTRACT

A tooth paste composition comprising black cumin oil (*Nigella sativa*) and fluoride-doped bioactive glass, zinc oxide, and/or titanium oxide is disclosed.

5 Claims, 5 Drawing Sheets

Negative Control

Positive Control

Experimental Paste A

Experimental Paste B

Experimental Paste C

Experimental Paste D

Untreated

METHOD FOR CONTROLLING DENTAL CARIES AND TREATING TEETH SENSITIVITY

CROSS-REFERENCE TO RELATED APPLICATIONS

The present application is a Continuation of U.S. application Ser. No. 16/252,039, now allowed, having a filing date of Jan. 18, 2019.

BACKGROUND OF THE INVENTION

Field of the Disclosure

This disclosure relates to a toothpaste composition comprising fluoride-doped bioactive particles having antibacterial activity.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Dental caries is an infectious disease induced by diet that results in the destruction of hard dental tissue [Harris et al. Risk factors for dental caries in young children: a systematic review of the literature, Community dental health 21 (1 Suppl) (2004) 71-85]. It affects 60-90% of school-aged children in most industrialized countries and a major portion of adults [Petersen et al. The global burden of oral diseases and risks to oral health, Bulletin of the World Health Organization 83 (2005) 661-669]. The surface of an infected tooth is covered with plaque consisting of a bacterial film which produces acids as byproducts of bacterial metabolism. Calcium phosphate mineral of tooth enamel or dentin is dissolved by acids in a process called demineralization. The other common disease related to oral cavity is periodontal disease which can be a hereditary or acquired disorder of the periodontium, i.e., tissues surrounding and supporting the teeth [Armitage, P. E. Periodontal diagnoses and classification of periodontal diseases, Periodontology 2000 34 (2004) 9-21]. Periodontal diseases are caused by plaque or biofilm which is the principal etiological factor leading to the diseases. Thus, plaque control is required for prevention of diseases related to plaque buildup. Plaque control is achieved by mechanical means and chemical treatment and carried out by self-care and/or hygienists or dentists [Axelsson et al. The long-term effect of a plaque control program on tooth mortality, caries and periodontal disease in adults. Results after 30 years of maintenance, Journal of clinical periodontology 31(9) (2004) 749-57]. Dentifrice, i.e., toothpaste, is used with a toothbrush to clean and/or polish the teeth. It aids the toothbrush in cleaning the teeth surfaces and as delivery vehicle for one or more therapeutic agents. Dentifrices are formulated with several ingredients including abrasive substances, surfactants, humectants, thickeners, flavoring agents, preservatives, colors, film agents, and sweeteners as well as one or more therapeutic agents effective in controlling plaque and gingivitis. The therapeutic agents may have an antimicrobial or anti-inflammatory activity to increase the efficacy of tooth brushing. The mechanical action of the toothbrush will decrease the amount of biofilm and disrupt its structure thereby providing direct access of the therapeutic agents to the tooth surface and surrounding tissues [Sanz et al. Antiplaque and antigingivitis toothpastes, Monographs in oral science 23 (2013) 27-44]. Fluoride, an anti-caries agent, is an essential component of toothpaste. Toothpaste typically contains an amount of fluoride in the range of 500 and 1,500 ppm in the form of sodium monofluorophosphate (MFP), sodium fluoride (NaF) or combination thereof. Also, toothpastes formulated with stannous fluoride ($SnF_2$) and amino fluoride (AmF) are known [Twetman et al. Caries-preventive effect of fluoride toothpaste: a systematic review, Acta odontologica Scandinavica 61(6) (2003) 347-55].

De-sensitizing toothpastes, mouthwashes, and chewing gums are employed for treatment of dentinal hypersensitivity (DH). It may be defined as short, sharp pain arising from exposed dentin in response to stimuli, typically thermal, evaporative, tactile, osmotic or chemical and which cannot be ascribed to any other dental defect or pathology [Holland et al. Guidelines for the design and conduct of clinical trials on dentine hypersensitivity, Journal of clinical periodontology 24(11) (1997) 808-13]. In recent years, various studies have shown hydroxyapatite nanoparticles (nano-HA) as a biomimetic material for re-constructing tooth enamel suffering from mineral loss. Because of its unique potential for remineralization, it has been considered as an effective anti-caries agent [Yamagishi et al. Materials chemistry: a synthetic enamel for rapid tooth repair, Nature 433(7028) (2005) 819, Li et al. Tang, Repair of enamel by using hydroxyapatite nanoparticles as the building blocks, Journal of Materials Chemistry 18(34) (2008) 4079-4084; Roveri et al. Surface Enamel Remineralization: Biomimetic Apatite Nanocrystals and Fluoride Ions Different Effects, Journal of Nanomaterials 2009 (2009) 9; and Hannig et al. Nanomaterials in preventive dentistry, Nature nanotechnology 5(8) (2010) 565-9]. Also, studies have reported the potential of nano-HA to remineralize artificial carious lesions following addition to toothpastes, mouthwashes, and other dental care products [Yamagishi et al. (2005), and Gao et al. Effect of nano-hydroxyapatite concentration on remineralization of initial enamel lesion in vitro, Biomedical materials (Bristol, England) 4(3) (2009) 034104].

Prof. L. L. Hench introduced the first bioactive glass in 1969 having the composition of 46.1 mol. % $SiO_2$, 24.4 mol. % $Na_2O$, 26.9 mol. % CaO and 2.6 mol. % $P_2O_5$ (later termed 45S5 and Bioglass®). Bioactive glass forms a strong bond with bone [Hench, L. L. The story of Bioglass®, Journal of Materials Science: Materials in Medicine 17(11) (2006) 967-978]. It has been incorporated into toothpastes because of its potential for remineralization and antibacterial properties as well as for the treatment of hypersensitivity [Abbasi et al. Bioactive Glasses in Dentistry: A Review, J Dent Biomater 2 (1) (2015) 1-9].

NovaMin® (NovaMin Technology, GlaxoSmithKline, Florida, UK) is a very fine Bioglass® particulate. It has a particle size of ~18 μm and is used as an active repair agent in toothpaste. It reduces dentin hypersensitivity by mineralizing tiny holes in the dentin [Jones, J. R. Review of bioactive glass: From Hench to hybrids, Acta biomaterialia 9(1) (2013) 4457-4486]. When these types of toothpastes are used, Bioglass® particles adhere to the dentin and form apatite layer that is similar in composition to enamel and block dentinal tubules leading to relieving pain for longer periods of time [Gillam et al. The effects of a novel Bioglass dentifrice on dentine sensitivity: a scanning electron microscopy investigation, Journal of oral rehabilitation 29(4) (2002) 305-13]. They are generally introduced into various toothpastes as very fine particles to provide calcium and phosphorus to the tooth surface [Madan et al. Tooth remineralization using bio-active glass-A novel approach, Journal of Advanced Dental Research 2(2) (2011) 45]. Various studies have shown the remineralization potential of bioactive glasses incorporated in toothpastes [Vollenweider et al. Remineralization of human dentin using ultrafine bioactive glass particles, Acta biomaterialia 3(6) (2007) 936-43; and Wang et al. The dentine remineralization activity of a desensitizing bioactive glass-containing toothpaste: an in vitro study, Australian dental journal 56(4) (2011) 372-81].

Toothpastes require a certain degree of abrasivity to perform the cleaning action. However, abrasivity of toothpastes needs to be moderated in order to prevent the wearing of underlying enamel and dentin. Thus, toothpaste manufacturers aim at minimizing hard tissue damage while maximizing cleaning efficiency [Joiner et al. Whitening toothpastes: effects on tooth stain and enamel, International Dental Journal 52 (S5) (2002) 424-430]. The wear produced by toothpastes, toothbrushes, and polishing pastes is defined as abrasion in contrast to tooth-to-tooth contact wear which is defined as attrition.

In addition to abrasive agents various types of natural and/or herbal products have been used in dentifrices including extracts from sanguinarine, chamomile, sage, rhatany, myrrh, echinacea, and peppermint. Sanguinarine, an alkaloid extracted from the plant *Sanguinaria canadensis* has low bactericidal activity, and in combination with zinc chloride can significantly reduce plaque and gingivitis [Sanz et al. (2013)].

It is therefore one object of the present disclosure to provide a new dentifrice (toothpaste) with both synthetic and herbal active ingredients having low abrasivity. The active ingredients have ability to remineralize the tooth structure and contain antibacterial properties.

BRIEF SUMMARY OF THE INVENTION

According to a first aspect, the present disclosure relates to toothpaste composition comprising:
(a) black cumin oil (*Nigella sativa*) in the range of 0.1 wt. % to 6 wt. %,
(b) an amount of water in the range of 33 wt. % to 36 wt. %;
(c) a surfactant in the range of 1 wt. % to 2 wt. %,
(d) a humectant in the range of 29 wt. % to 32 wt. %,
(e) a preservative in the range of 0.5% to 1.0 wt. %,
(f) a thickening agent in the range of 0.5% to 1.0 wt. %,
(g) an abrasive agent in the range of 24 wt. % to 27 wt. %, and
(h) a flavoring agent in the range of 0.5% to 1.0 wt. %;
wherein the wt. % is the percent by weight of the total weight of the toothpaste.

In a preferred embodiment, the toothpaste comprises fluoride-doped bioactive glass in the range of 0.1 wt. % to 4.0 wt. % of the total weight of the tooth paste.

In another preferred embodiment, the toothpaste comprises an amount zinc oxide in the range of 0.1 wt. % to 3.0 wt. % of the total weight of the tooth paste.

In another preferred embodiment, the toothpaste comprises titanium oxide and zinc oxide in an amount in the range of 0.1 wt. % to 2.0 wt. % and fluoride-doped bioactive glass in an amount in the range of 0.1 to 4.0 wt. % of the total weight of the toothpaste.

In another preferred embodiment, the toothpaste comprises water in an amount of about 36 wt. % of the total weight of the total weight of the toothpaste.

In another preferred embodiment, the surfactant is sodium lauryl sulfate (SLS) in an amount in the range of 1 wt. % to 2 wt. % of the total weight of the toothpaste.

In another preferred embodiment, the humectant is glycerol in an amount of in the range of 29 wt. % to 32 wt. % of the total weight of the toothpaste.

In another preferred embodiment, the preservative is sodium benzoate in an amount of about 1 wt. % of the total weight of the toothpaste.

In another preferred embodiment, the thickening agent is methylcellulose in an amount in the range of 0.5 wt. % to 1 wt. % of the total weight of the toothpaste.

In another preferred embodiment, the abrasive agent is calcium carbonate in an amount in the range of 24 wt. % to 27 wt. % of the total weight of the toothpaste.

In a more preferred embodiment, the toothpaste composition comprises flavoring agent in an amount of about 1 wt. % of the total weight of the toothpaste.

In a more preferred embodiment, the toothpaste composition comprises:
black cumin oil (*Nigella sativa*) in the range of 0.1 wt. % to 6 wt. %,
an amount of water in the range of 33 wt. % to 36 wt. %;
sodium lauryl sulfate (SLS) in the range of 1 wt. % to 2 wt. %,
glycerol in the range of 29 wt. % to 32 wt. %,
sodium benzoate in the range of 0.5% to 1.0 wt. %,
methyl cellulose in the range of 0.5% to 1.0 wt. %,
calcium carbonate in the range of 24 wt. % to 27 wt. %,
flavoring agent in the range of 0.5% to 1.0 wt. %,
fluoride-doped bioactive glass in the range of 0.1 wt. % to 4.0 wt. %,
zinc oxide in an amount in the range of 0.1 wt. % to 3.0 wt. %, and
titanium oxide in an amount in the range of 0.1 wt. % to 3.0 wt. %;
wherein the wt. % is the present by weight of the total weight of the toothpaste.

According to the second aspect of invention, the disclosure is directed to a method of controlling dental caries and treating teeth sensitivity comprises: contacting the teeth of a subject with the tooth paste disclosed herein and brushing the teeth.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
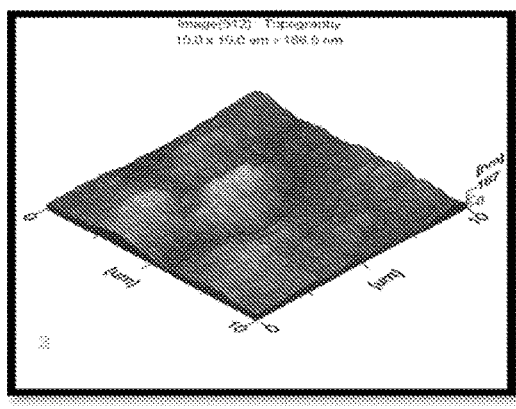
FIG. 1A shows dentine surface roughness observed by 3D-Atomic Force Microscope (AFM) for a negative control dentine treated with distilled water.
Figure 1B:
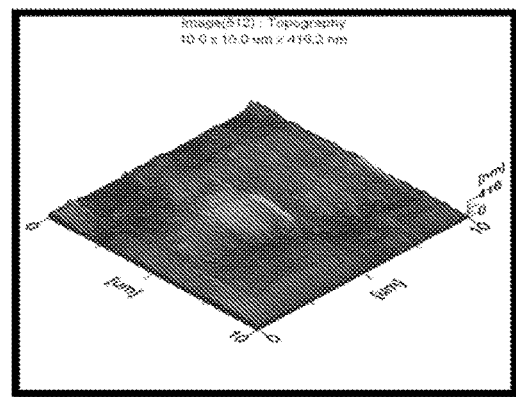
FIG. 1B shows dentine surface roughness observed by 3D AFM for a positive control dentine treated with commercial toothpaste.
Figure 1C:
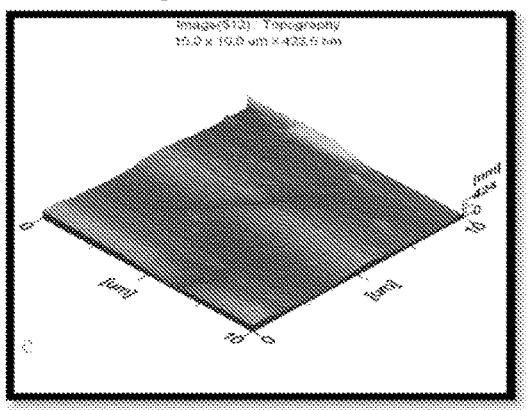
FIG. 1C shows dentine surface roughness observed by 3D AFM for a dentine treated with experimental past A.
Figure 1D:
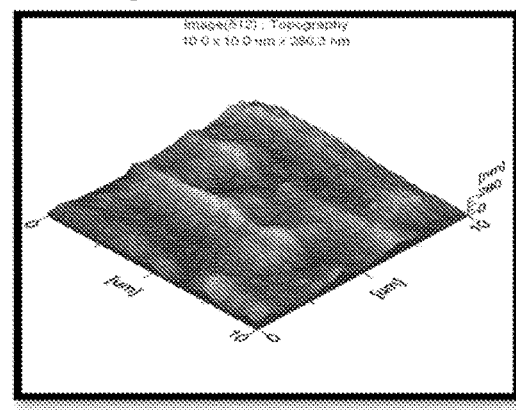
FIG. 1D shows dentine surface roughness observed by 3D AFM for a dentine treated with experimental past B.
Figure 1E:
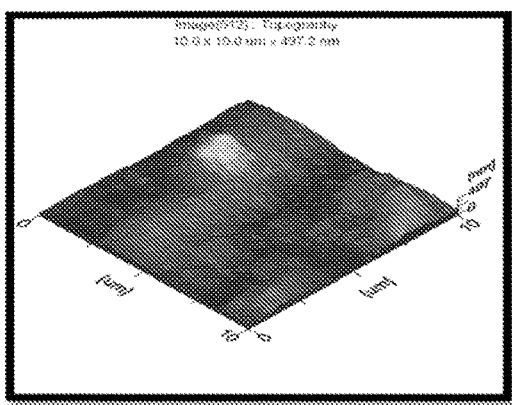
FIG. 1E shows dentine surface roughness observed by 3D AFM for a dentine treated with experimental past C.
Figure 1F:
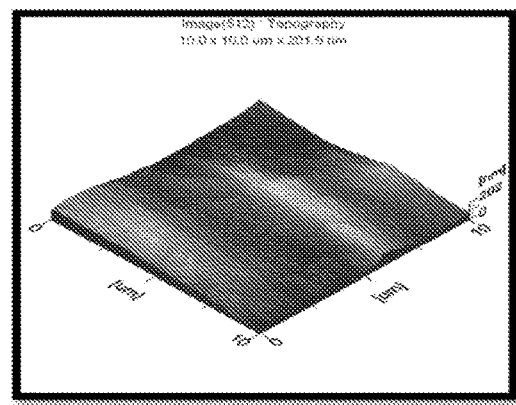
FIG. 1F shows dentine surface roughness observed by 3D AFM for a dentine treated with experimental past D.
Figure 1G:
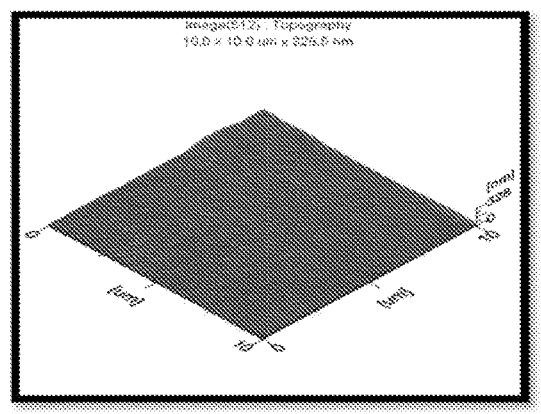
FIG. 1G shows dentine surface roughness observed by 3D AFM for a dentine untreated.

All publications mentioned herein are incorporated herein by reference in full for the purpose of describing and disclosing the methodologies, which are described in the publications, which might be used in connection with the description herein. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising" "include," "includes," and "including" are interchangeable and not intended to be limiting.

The terminology used herein is for the purpose of describing particular embodiments only and is not intended to be limiting of the invention.

The headings such as "Background" and "Summary", and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

As used herein, the term "and/or" includes any and all combinations of one or more of the associated listed items and may be abbreviated as "/".

The terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total weight of toothpaste, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Disclosure of values and ranges of values for specific parameters (such as temperatures, molecular weights, weight percentages, etc.) are not exclusive of other values and ranges of values useful herein. Two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it is also envisioned that Parameter X may have other ranges of values including 1-9, 2-9, 3-8, 1-8, 1-3, 1-2, 2-10, 2.5-7.8, 2-8, 2-3, 3-10, and 3-9, as mere examples.

Although the open-ended term "comprising," as a synonym of terms such as including, containing, or having, is use herein to describe and claim the present invention, the invention, or embodiments thereof, may alternatively be described using more limiting terms such as "consisting of" or "consisting essentially of" the recited ingredients. Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

A first aspect of the invention is directed a toothpaste composition comprises water, surfactant, humectant, thickening agent, abrasive agent, preserving agent, and flavoring agent. Also, the toothpaste composition may contain other ingredients such as but not limited to coloring agent, anticalculus agent, vitamins, sweetener, enzymes such as proteases and amylases, antioxidant, silicones, desensitizer such as potassium nitrate, whitening agent such as hydrogen peroxide, calcium peroxide, urea peroxide, clay, breath freshening agent, antibacterial, antiplaque agent, Poloxomer polymers such as POLOXOMER 407, PLURONIC F108, (both available from BASF Corporation), polymers, polyglycoside (APG), chlorophyll compound, bicarbonate salts, and viscosity modifier. Also, basic amino acids such as but are not limited to arginine, lysine, citrulline, ornithine, creatine, histidine, diaminobutanoic acid, diamine propionic acid, salts thereof and combinations thereof may be included in the toothpaste.

The toothpaste composition of the invention comprises water in an amount in the range of 20% to 50%, preferably in the range of 25 to 40%, more preferably in the range 30% to 38%, and most preferably about 36% by weight of the total weight of the toothpaste composition and at least one surfactant.

The surfactant is useful for example to compatibilize other components of the composition and thereby provide enhanced stability as well as to aid in cleaning the dental surface through detergency and provide foam upon agitation, e.g., during brushing with a dentifrice composition of the invention. Any orally acceptable surfactant, most of which are anionic, cationic, nonionic, zwitterionic, or amphoteric, or mixture thereof can be used.

Suitable anionic surfactants include without limitation water-soluble salts of $C_{8-20}$ alkyl sulfates, sulfonated monoglycerides of $C_{8-20}$ fatty acids, sarcosinates, taurates, and the like. Illustrative examples of these and other classes include sodium dodecyl benzene sulfonate, sodium lauryl sulfate, sodium ether lauryl sulfate, sodium coconut monoglyceride sulfonate, sodium lauryl sarcosinate, sodium lauryl isoethionate, sodium laureth carboxylate, and sodium dodecyl benzenesulfonate.

Suitable cationic surfactants useful in the oral compositions of the present invention can be broadly defined as quaternary ammonium compounds having one long alkyl chain containing from about 8 to about 18 carbon atoms such as lauryl trimethylammonium chloride; cetyl pyridinium chloride; cetyl trimethylammonium bromide; di-isobutylphenoxyethoxyethyl-dimethylbenzylammonium chloride; coconutalkyltrimethylammonium nitrite; cetyl pyridinium fluoride; etc. Especially preferred are the quaternary ammonium fluorides described in U.S. Pat. No. 3,535,421 incorporated by reference hereinbefore in its entirety, where said quaternary ammonium fluorides have detergent properties.

Suitable nonionic surfactants include without limitation poloxamers such as POLOXOMER 407 and PLURONIC F108 (both available from BASF Corporation), polyoxyethylene sorbitan esters, fatty alcohol ethoxylates, alkylphenol ethoxylates, tertiary amine oxides such as but not limited to dodecyldimethylphosphine oxide, tetradecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxy-propyldi(2-hydroxyethyl)phosphine oxide, stearyldimethylphosphine oxide, cetylethylpropyl-phosphine oxide, oleyldiethylphosphine oxide, dodecyldiethylphosphine oxide, tetradecyldiethylphosphine oxide, dodecyldipropyiphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide, tertiary phosphine oxides such as but not limited to dodecyldimethylphosphine oxide, tetradecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxy-propyldi(2-hydroxyethyl)phosphine oxide, stearyldimethylphosphine oxide, cetylethyl-propylphosphine oxide, oleyldiethylphosphine oxide, dodecyldiethylphosphine oxide, tetradecyldiethylphosphine oxide, dodecyldipropyiphosphine oxide, dodecyldi(hydroxyl-methyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide, dialkyl sulfoxides such as but not limited to octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxy propyl sulfoxide, tetradecyl methyl sulfoxide, 3-methoxytridecyl methyl sulfoxide 3-hydroxytridecyl methyl sulfoxide, 3-hydroxy-4-dodecoxybutyl methyl sulfoxide and the like.

Zwitterionic synthetic detergents useful in the oral compositions of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water solubilizing group, e.g., carboxy, sulfonate, sulfate, phosphate, or phosphonate. Examples include: 4-[N,N-di(2-hydroxyethyl)-N-octadecylammonio]-butane-1-carboxylate; 5-]S-3-hydroxy-propyl-S-hexadecylsulfonio]-3-hydroxypentane-1-sulfate; 3-[P,P-diethyl-P-3,6,9-trioxatetradecoxylphosphonio]-2-hydroxypropane-1-phosphate; 3-[N,N-dipropyl-N-3-dodecoxy-2-hydroxypropylammonio]-propane-1-phosphonate; 3-(N,N-dimethyl-N-hexa-decylammonio)propane-1-sulfonate; 3-(N,N-dimethyl-N-hexadecylammonio)-2-hydroxy-propane-1-sulfonate; 4-[N,N-di(2-hydroxy ethyl)-N-(2-hydroxydodecyl)ammonio]butane-1-carboxylate; 3-[S-ethyl-S-(3-dodecoxy-2-hydroxypropyl)sulfonio]-propane-1-phosphate; 3-[-P,P-dimethyl-P-dodecylphosphonio]-propane-1-phosphonate; and 5-[N,N-di(3-hydroxypropyl)-N-hexadecylammonio]2-hydroxypentane-1-sulfate.

Suitable amphoteric surfactants include without limitation derivatives of $C_{8-20}$ aliphatic secondary and tertiary amines having an anionic group such as carboxylate, sulfate, sulfonate, phosphate or phosphonate. Examples of compounds falling within this definition are sodium 3-dodecylaminopropionate, sodium 3-dodecylaminopropane sulfonate, dodecyl-beta-alanine, cocoamidopropyl betaine, N-alkyl-taurines such as the one prepared by reacting dodecylamine with sodium isethionate according to the teaching of U.S. Pat. No. 2,658,072, N-higher alkyl aspartic acids such as disclosed in U.S. Pat. No. 2,438,091, and the products sold under the trade name "Miranol" and described in U.S. Pat. No. 2,528,378.

The amount of one or more surfactants are present in a total amount in the range of 0.01% to 10%, preferably in the range of 0.05% to 5%, more preferably 1.0% to 4.0%, and most preferably in the range of 1.5% to 2.5% by weight of the total weight of the toothpaste composition.

In a preferred embodiment, the toothpaste composition comprises sodium lauryl sulfate (SLS) in an amount in the range of 0.1% to 10%, and preferably in the range of 0.5% to 5%, more preferably in the range of 1.0 to 3%, and most preferably about 2% by weight of the total weight of toothpaste composition.

Also, the toothpaste composition of the invention comprises at least one thickening agent, useful for example to impart a desired consistency and/or mouth feel to the composition. Any orally acceptable thickening agent can be used, including without limitation carbomers, also known as carboxyvinyl polymers, carrageenans, also known as Irish moss, and more particularly t-carrageenan (iota-carrageenan), cellulosic polymers such as methylcellulose, hydroxyethyl-cellulose, carboxymethylcellulose (CMC) and salts thereof, e.g., CMC sodium, natural gums such as karaya, xanthan, gum Arabic and tragacanth, colloidal magnesium aluminum silicate, colloidal silica and the like. One or more thickening agents are present in a total amount in the range of 0.01% to 10%, preferably in the range of 0.1% to 5%, more preferably in the range of 0.2% to 1.5%, and most preferably 0.5% to 1.0% by weight of the total weight of the toothpaste composition.

In a preferred embodiment, the toothpaste composition comprises methylcellulose in an amount in the range of 0.01% to 10%, preferably in the range of 0.1% to 5%, more preferably in the range of 0.2% to 1.5%, and most preferably 0.5% to 1.0% by weight of the total weight of the toothpaste composition. In a particularly preferred embodiment, the toothpaste composition comprises about 1% by weight of the total composition of the toothpaste composition.

In another preferred embodiment, the toothpaste composition of the invention comprises at least one humectant, useful for example to prevent hardening of toothpaste upon exposure to air. Any orally acceptable humectant can be used, including without limitation polyhydric alcohols such as glycerin, sorbitol, xylitol, butylene glycol, propylene glycol, polyethylene glycol, other edible polyhydric alcohol, or low molecular weight PEGs, and combinations thereof.

Also, most humectants function as sweeteners. A humectant is present in the composition in an amount in the range of 5% to 60%, preferably in the range of 10% to 50%, more preferably in the range of 20% to 35%, and most preferably in the range of 25% to 33% by weight of the total weight of the toothpaste composition. In a particularly preferred embodiment, the humectant is glycerol added to the toothpaste composition in an amount in the range of 29% to 32%, preferably about 32% by weight of the total weight of the toothpaste composition.

In another preferred embodiment, the toothpaste composition of the invention comprises at least one abrasive, useful for example as a polishing agent. Any orally acceptable abrasive can be used, but type, particle size and amount of abrasive should be selected so that tooth enamel is not excessively abraded in normal use of the composition. Suitable abrasives include without limitation silica, for example in the form of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates, and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate. In a particularly preferred embodiment, calcium carbonate is used alone or in combination with other suitable abrasive material. The abrasive is present in the toothpaste compositing in an effective amount, typically in the range of 10% to 60%, preferably in the range of 15% to 40%, more preferably in the range 20% to 30%, and most preferably in the range 24% to 27% of by weight of the total weight of the toothpaste composition. Average particle size of an abrasive is generally in the range of 0.1 to 30 µm, preferably I the range of 1 to 20 µm, and more preferably in the range of 5 to 15 µm.

In a particularly preferred embodiment, the abrasive is calcium carbonate added to the toothpaste composition in an amount in the range of 20% to 35%, preferably in the range 25% to 30%, more preferably in the range of 26% to 28%, and most preferably about 27% by weight of the total weight of the toothpaste composition.

In some embodiments, the toothpaste composition of the invention comprises at least one bicarbonate salt, useful for example to impart a "clean feel" to teeth and gums due to effervescence and release of carbon dioxide. Any orally acceptable bicarbonate can be used, including without limitation alkali metal bicarbonates such as sodium and potassium bicarbonates, ammonium bicarbonate and the like. One or more bicarbonate salts are optionally present in a total amount in the range of 0.1% to 20%, preferably in the range of 2% to 10% by weight of the total toothpaste composition.

In some embodiments, the toothpaste composition of the invention comprises at least one pH buffering agent in sufficient amount to maintain the pH of the composition at a desired level. The buffering agent is a combination of acid or base and a salt thereof. Many examples buffering agents are well known in the art having good pH buffering capacity in the pH range of 2.0 to 10.0 including but not limited to citrate, tartrate, acetate, phosphate, glycine, carbonate, borate, and imidazole.

In some embodiments, the toothpaste composition of the invention contains one or more flavoring agent, useful for example to enhance taste of the composition. Any orally acceptable natural or synthetic flavoring agent may be used, including, but not limited to, vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, bean- and nut-derived flavors such as coffee, cocoa, cola, peanut, and almond as well as. Also encompassed within flavoring agents herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, .α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA), natural or artificial sweetener including but not limited to non-cariogenic sweeteners such as saccharin, aspartame, dextrose, and levulos, and the like. The toothpaste composition of the invention comprises one or more flavoring agents in a total amount in the range of 0.01% to 5%, preferably in the range of 0.1% to 3%, more preferably in the range of 0.5 to 1.5%, and most preferably about 1%.

The toothpaste composition may contain one or more anticalculus agents. Suitable anticalculus agents include, but are not limited to, phosphates and polyphosphates such as pyrophosphates, polyaminopropanesulfonic acid (AMPS), zinc citrate trihydrate, polypeptides such as polyaspartic and polyglutamic acids, polyolefin sulfonates, polyolefin diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. A particularly useful inorganic phosphate and polyphosphate salts include, but not limited to monobasic, dibasic and tribasic sodium phosphates, sodium tripolyphosphate, tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful anticalculus agents include anionic polycarboxylate polymers. The anionic polycarboxylate polymers contain carboxyl groups on a carbon backbone and include polymers or copolymers of acrylic acid, methacrylic, and maleic anhydride. Non-limiting examples include polyvinyl methyl ether/maleic anhydride (PVME/MA) copolymers, such as those available under the Gantrez brand from ISP, Wayne, N.J. Still other useful anticalculus agents include sequestering agents including di and tricarboxylic acids and hydroxycarboxylic acids such as citric, fumaric, malic, glutaric and oxalic acids and salts thereof, and aminopolycarboxylic acids such as ethylenediaminetetraacetic acid (EDTA). One or more anticalculus agents may be present in the toothpaste composition in an anticalculus effective total amount, typically in the range of 0.01% to 20%, preferably in the range of 0.1 to 15%, more preferably in the range of 1% to 10% by weight of the total toothpaste composition.

Another useful additive to the toothpaste composition is a viscosity modifier, useful for example to inhibit settling or separation of ingredients or to promote re-dispensability upon agitation of a liquid composition. Any orally acceptable viscosity modifier can be used, including without limitation mineral oil, petrolatum, clays, organo-modified clays, silica, and the like. One or more viscosity modifiers may be added to the toothpaste composition in an amount in the range of 0.01% to 10%, preferably in the range of 0.1% to 5% by weight of the total weight of the toothpaste composition.

An orally acceptable breath freshening agent is yet another useful additive to the toothpaste composition. One or more such agents may be added to the toothpaste composition in an effective amount. Suitable breath-freshening agents include, but not limited to zinc salts such as zinc gluconate, zinc citrate and zinc chlorite, α-ionone and the like.

Preservatives, such as sodium benzoate, butylated hydroxyanisole (BHA), butylated hydroxytoluene (BHT), p-hydroxybenzoic ester, ascorbic acid, alkyldiaminoethylglycine hydrochloride, chlorhexidine, triclosan, quaternary ammonium compounds such as benzalkonium chloride, benzyl alcohol, tocopherol, or parabens such as methyl, ethyl or propyl paraben may be incorporated in the toothpaste composition. The amount of preservative in the toothpaste composition is typically in the range of 0.1 wt. % to about 2 wt. %, preferably in the range of 0.2 wt. % to 1.5 wt. %, more preferably in the range of 0.5 wt. % to 1.2 wt. % and most preferably about 1% of the total weight of the toothpaste composition.

As used herein, the term "active ingredient" refers to an ingredient that has a specific function in treating and restoring the dentin and gum. For example, black cumin oil from *Nigella sativa* has antibacterial, anti-inflammatory, and anti-oxidant activities. Fluoride-doped bioactive glass has both antibacterial and remineralization activities. Zinc oxide has antibacterial and remineralization activity. Titanium oxide is whitening agent.

*Nigella sativa* (commonly known as black cumin, black seed, or black curcumin) is an annual flowering plant, native to south and southwest Asia. It grows to 20-30 cm (7.9-12 in) tall, with finely divided, linear but not thread-like leaves. The flowers are delicate, and usually colored pale blue and white, with five to ten petals. The fruit is a large and inflated capsule composed of three to seven united follicles, each containing numerous seeds. The seed may be used as a spice. *Nigella sativa* has a pungent bitter taste and smell. *Nigella sativa* is traditionally used in the Indian subcontinent, the Middle East, and Europe for culinary and medicinal purposes as a natural remedy for a number of illnesses and conditions that include asthma, hypertension, diabetes, inflammation, cough, bronchitis, headache, eczema, fever, dizziness and influenza. Much of the biological activity of the seeds is believed to be due to thymoquinone (TQ), the putative active phytochemical of *Nigella sativa*, a component of the essential oil. TQ is also present in the fixed oil. Also, *Nigella sativa* oil contains conjugated linoleic (18:2) acid, nigellone (dithymoquinone), melanthin, nigilline, damascenine, and tannins.

Extracts and oil obtained from *Nigella sativa* are known to have antimicrobial activity, anti-inflammatory activity and anti-oxidant activity and have been used as additives to dental care products (US2014/0308219-incorporated in its entirety herein by reference). Also, known is the addition of oil from *Nigella sativa* to toothpaste compositions lubricates mouth tissues and/or treats dry mouth. In addition, when components found in extracts of *Nigella sativa*, or oils from *Nigella sativa* are added to dentifrice compositions, the astringency of the compositions is reduced. Accordingly, one of the main active ingredients used in the toothpaste of the disclosed invention is an extract or black cumin oil from *Nigella sativa*. The extract or oil is added to the total toothpaste in an amount in the range of 0.01% to 10%, preferably in the range 1% to 9%%, more preferably in the range 1.5% to 7%, and most preferably in the range of 2% to 6% by weight of the total weight of the toothpaste. In a preferred embodiment, black cumin oil from *Nigella sativa* is add to the toothpaste composition in an amount in the range of 0.5% to 6% by weight of the total weight of the toothpaste.

As referred to herein, an "extract" or "oil" suitable for use in the various embodiments of the present invention can be obtained from any part of *Nigella sativa* plant including the leaf, stem, stalk, cortex (i.e., bark), pulp, seed, flesh, juice, root, flower, or any other suitable part of a plant or other natural source.

As used herein, "extracting" or "extraction" of a solid or liquid material means contacting the material with an appropriate solvent to remove the substance(s) desired to be extracted from the material. Where the material is solid, it is preferably dried and crushed or ground prior to contacting it with the solvent. Such an extraction may be carried out by conventional means known to one of skill in the art, for example, by using an extraction apparatus, such as a Soxhlet apparatus, which retains the solid material in a holder and allows the solvent to flow through the material; by blending the solvent and material together and then separating the liquid and solid phases or two immiscible liquid phases, such as by filtration or by settling and decanting. In various embodiments, the botanical active ingredients used in oral care compositions are of reproducible, stable quality and have microbiological safety. Black cumin oil from *Nigella sativa* may be obtained commercially or by extracting the oil from the plant seeds by well-known methods in the art.

"Bioactive glass" refers to a group of surface reactive glass-ceramics that include the original bioactive glass, Bioglass®. The biocompatibility of these glasses has led them to be investigated extensively for use as implant materials in the human body to repair and replace diseased or damaged bone. There have been many variations on the original composition which was FDA approved and termed Bioglass®, which is also known as 45S5. As referred to herein, bioactive glasses are typically silicon dioxide-based compositions capable of forming hydroxycarbonate apatite when exposed to physiological fluids. Typically, the bioactive glasses for use in the presently disclosed compositions and methods have the following composition by molar percentage:

from about 50 to about 96 mole percent $SiO_2$;
from about 2 to about 50 mole percent CaO;
from about 2 to about 16 mole percent $P_2O_5$;
from about 0 to about 25 mole percent $CaF_2$; and
from about 0 to about 10% $B_2O_3$, or an equivalent.

Examples of commercially available bioactive glass and their chemical composition include, but not limited to, 45S5: 46.1 mol % $SiO_2$, 26.9 mol % CaO, 24.4 mol % $Na_2O$ and 2.5 mol % $P_2O_5$; 58S: 60 mol % $SiO_2$, 36 mol % CaO, and 4 mol % $P_2O_5$; S70C30: 70 mol % $SiO_2$, and 30 mol % CaO, 8.4% $Na_2O$, 40.6% CaO, 39% SiO2, and 12% P2O5.

In one embodiment, the Bioglasses used in the disclosed composition and methods have the following composition:

$SiO_2$ in the range of 35 wt. % to 55 wt. %, preferably in the range of 38 to 50 mole percent, more preferably in the range 42 wt. % to 47 wt. %, and most preferably 44 wt. % to 46 wt. %;

CaO in the range of 15 wt. % to 40 wt. %, more preferably in the range of 18 wt. % to 35 wt. %, more preferably in the range of 22 to 28 wt. %, and most preferably 23 wt. % to 26 wt. %;

$Na_2O$ in the range of 15 wt. % to 40 wt. %, more preferably in the range of 18 wt. % to 35 wt. %, more preferably in the range of 22 to 28 wt. %, and most preferably 23 wt. % to 26 wt. %; and $P_2O_5$ in the range of 2 wt. % to 10 wt. %, more preferably in the range of 3 wt. % to 9 wt. %, more preferably in the range of 4 wt. % to 8 wt. %, and most preferably 5 wt. % to 7 wt. %.

In a particularly preferred embodiment, the Bioglass has the composition 45 wt % SiO2, 24.5 wt % CaO, 24.5 wt % Na2O, and 6.0 wt % P2O5.

Thomas et al. [J Long Term Eff Med Implants (2005) 15(6):585-97—incorporated herein by reference in its entirety] review different bioactive glass materials and their uses. The bioactive glass compositions suitable for use in accordance with the present disclosure are not limited to the particular examples provided, but include other bioactive glass materials such as those known in the art. Many bioactive glass compositions are also disclosed in U.S. Pat. Nos. 5,735,942; 6,054,400; 6,171,986; 6,517,857; 9,168,272; and 10,111,814—incorporated herein by reference in their entirety.

Bioactive and biocompatible glasses have been developed as bone replacement materials. Studies have shown that these glasses will induce or aid osteogenesis in physiologic systems. The bond developed between the bone and the glass has been demonstrated to be extremely strong and stable. However the size of the particles used to form bone is relatively large. Tooth dentin is very different from bone. The organic component of dentin (approximately 40%) makes most systems that will bond to bone and tooth enamel ineffective. Most current materials used for treatment of tooth desensitization rely on materials that have been optimized for the bonding to bone and tooth enamel by their interaction with the inorganic components. As a result, even the most effective treatments are short lived. Therefore, there is a need in the dental field for a material that would chemically react with and/or passivates the surface of dentin and intimately bonds or adheres to tooth structure, and functions to reduce the reopening of dentin tubules due to contact with oral fluids.

The bioactive glass used in the toothpaste composition of the invention is doped with a fluoride compound such as calcium fluoride, sodium monofluorophosphate (MFP), stannous fluoride, sodium fluoride or combination thereof. The fluoride-doped bioactive glass comprises a fluoride compound in an amount in the range of 0.5 mol. % to 12 mol. %, preferably in the range of 1 mol. % to 10 mol. %, more preferably in the range of 2 mol. % to 7 mol. %, and most preferably 3 mol. % to 6 mol. %. In a particularly preferred embodiment, the Bioglass contains about 5 mol. % of the fluoride compound. The toothpaste composition of the invention contains fluoride-doped bioglass in an amount in the range of 0.1% to 8%, preferably in the range of 0.5% to 6%, more preferably in the range of 1% to 5% and most preferably in the range of 1% to 4% by weight of the total weight of the toothpaste.

The compositions comprising fluoride-doped bioactive glass disclosed herein provide for mechanical and chemical obturation of enamel tubules as well as anti-caries fluoride ion. Moreover, in certain embodiments, the present compositions and methods optionally provide a bioactive layer doped with fluoride forming a new structural layer which results in long-lasting reduction of tooth hypersensitivity and may function to slowly release the anti-caries fluoride ion to minimize the bacterial population in the mouth. Such structured layers have been observed by the reformation of a hydroxycarbonate apatite layer on and in dentin surfaces after treatment with composition comprising bioglass (see for example US2007/0258916—incorporated herein by reference in its entirety). Particles that are small enough to fit inside or rest on the opening of the tubules provide for actual physical occlusion of the tubules. Thus, embodiments of the disclosed compositions include particles smaller than 90 microns, such particles are more likely to adhere to the tubules or tooth surface because particles less than about 90 microns react quickly enough to chemically bond with dentin surfaces and tubules during the use of the disclosed compositions, including toothpastes, gels or mouthwashes.

In certain disclosed compositions, the bioglass particles have an average diameter of less than about 50 microns, such as less than about 20 microns and may fall into a range of from about 0.1 micron to about 10 microns, such as an average diameter of about 2 microns. In some embodiments the compositions include particles of many sizes but have at least about 25% of the particles having a diameter of less than about 5 microns, such as less than about 2 microns.

As used herein the phrase "coloring agent" is an agent that imparts not only color to the toothpaste, but also provides a particular luster or reflectivity such as pearling agents and whiting agents. Coloring agents include, but not limited to, pigments and dyes. A coloring agent may serve a number of functions, including for example to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including without limitation talc, mica, magnesium carbonate, calcium carbonate, magnesium silicate, magnesium aluminum silicate, silica, titanium dioxide, red, yellow, brown and black iron oxides, ferric ammonium ferrocyanide, manganese violet, ultramarine, titaniated mica, bismuth oxychloride and the like. One or more coloring are optionally present in a total amount by weight in the range of 0.001% to 10%, preferably in the range of 0.01% to 5%, more preferably in the range of 0.1% to 3% of the total weight of the toothpaste composition.

In a particularly preferred embodiment, the coloring agent is the whitening agent titanium oxide added to the toothpaste composition in an amount in the range of 0.01 to 5%, preferably in the range of 0.1 to 4%, more preferably in the range of 0.5 to 3%, and most preferably in the range of 1.0 to 2% by weight of the total weight of the toothpaste composition.

A second aspect of the invention is directed to a method of treating and or controlling teeth hypersensitivity and carries. The method comprises contacting the toothpaste of the invention with teeth and gum, and brushing the teeth one or more time per day, preferably at least 2 times/day, more preferably at least 4 times/day, and most preferably at least 5 times per day. In a particularly preferred embodiment, the method should be carried out after every meal and before bedtime. The toothpaste composition should be applied with brushing for at least one minute, preferably two at least two minutes, and more preferably for at least three minutes. Not only may the method be used in treatment of hypersensitivity of the teeth, but also in a maintenance protocol to insure the long term health of the teeth and gum by preventing plaque buildup. The protocol may include the use of mouth wash after and/or before the application of the toothpaste and frequent visits to a dentist office for removal of any accumulated dental plaque and monitoring the health of the teeth.

EXAMPLE 1

Materials:

The chemicals used were analytical grade. Table 1 lists ingredients of the basic composition and the active ingredients as well as their quantities to formulate dentifrices.

TABLE 1

An Exemplary Composition of Basic and active ingredients

| Ingredients of basic Composition | wt. %[1] |
|---|---|
| Water | 36 |
| Sodium Lauryl Sulfate (SLS) | 2 |
| Glycerol | 32 |
| Sodium Benzoate | 1 |
| Methylcellulose | 1 |
| Calcium Carbonate | 27 |
| Peppermint (Flavoring Agent) | 1 |

| Active Ingredient | wt. %[2] |
|---|---|
| Zinc oxide (Nano-powders) (Antibacterial/Remineralization) | 0-3 |
| Fluoride-doped bioactive glass (Remineralization) | 0-4 |
| Titanium dioxide (Whitening) | 0-2 |
| Black cumin oil (Nigella sativa) (Antibacterial/Anti-inflammatory) | 0-6 |

[1]Percentage by weight of ingredient in the total weight of the basic composition.
[2]Percentage by weight of an active ingredient in the total weight of the final composition.

Methods:

A mixture of basic ingredients was prepared. Active ingredients were added to the mixture of basic ingredients and mixed for sufficient time to insure homogeneity of the mixture. The ratios of the active ingredients are varied to determine the effective amount of each ingredient. The mixing procedure was conducted at ambient temperature i.e. 23±2° C. One commercial dentifrice i.e. Colgate Cavity Protection (Colgate Palmolive) was used as a reference dentifrice and it contains sodium monofluorophosphate 0.76% (0.15% w/v fluoride ion) and dicalcium phosphate dehydrate and was denoted as CT. Table 2 summarizes the composition of the toothpastes tested.

TABLE 2

Composition of the Toothpaste

| Experimental toothpaste | Composition | Active ingredient[2] |
|---|---|---|
| EXT-A | [1]Basic composition | 1.5 wt. % n-fluoride-doped bioglass containing 5 wt. % fluoride. 3 wt. % n-ZnO. 3 wt. % Black seed oil. |
| EXT-B | [1]Basic composition | 1.5 wt. % n-fluoride-doped bioglass containing 5 wt. % fluoride. 3 wt. % n-ZnO. 3 wt. % Black seed oil. |

TABLE 2-continued

Composition of the Toothpaste

| Experimental toothpaste | Composition | Active ingredient[2] |
|---|---|---|
| EXT-C | [1]Basic composition | 1.5 wt. % n-fluoride-doped bioglass containing 5 wt. % fluoride. 3 wt. % n-ZnO. 3 wt. % Black seed oil. |
| EXT-D | [1]Basic composition | None |
| CT | Active | Dicalcium phosphate dehydrate |

[1]the basic composition is shown in Table 1.
[2]The wt. % is the percentage by weight of the active ingredient in the total weight of the toothpaste composition.

Teeth Preparation:

Freshly extracted bovine teeth were collected and extracted from cattle having an age in the range of 30-72 months old. The age was assessed according to Food Safety and Inspection Service (FSIS) standard operating procedures. All crowns surfaces were intact without cracks, fractures, and occlusal wear. Teeth were scraped clean from soft tissue remnants using a scalpel and currete. Disinfection was performed with 5% sodium hypochlorite for 24 h. Samples were stored in sterile 0.9% saline (ISO 11609: 2010) and were stored at 4° C. with 0.5% thymol solution in order to maintain the mineral content of tooth samples.

Sample Preparation:

Total 60 teeth specimens (4 mm×4 mm×2 mm; length, width and height respectively) were prepared from bovine incisors. The crown portions of the teeth were sectioned at cementum-enamel junction with a bur under continuous flow of water. Coronal portion was used for dentin samples. Specimens were prepared from buccal aspect of the teeth. Water-cooled diamond bur or disc (MANI, INC. 8-3 Kiyohara Industrial Park, Utsunomiya, Tochigi, Japan) were used for cutting. Plus mark was made at the back of each tooth with straight fissure bur in order to recognize the buccal aspect of the tooth. Samples were mounted in the impression compound and were labeled after randomly dividing the samples into six groups. The specimens were etched with 37% phosphoric acid for 30 s as per specification guidelines, washed and sonicated in distilled water for 30 s in order to remove residual particles without affecting the structure.

Preparation of Reference and Test Paste Slurries:

Reference and test paste slurries were prepared by adding 40 mL of distilled water to 25 g of each dentifrice (ISO 11609:2010) and stirred with a magnetic stirrer. The prepared dentin samples were randomly divided into 6 groups (n=10). Each tooth was coated with two layers of acid resistant nail varnish (Max Factor International, Procter & Gamble Ltd. Surrey, England) except for an exposed dentin window on the buccal surface.

Testing Apparatus: Brushing Machine:

A custom made tooth brush with six brushing heads, variable speed, and load was used in accordance with the ISO standards (ISO 11609:2010). It was used to duplicate the effects of brushing on teeth. The simulator allowed for accelerated brushing that replicated many years of regular tooth brushing. The samples were subjected to brushing conditions that closely resemble the mechanical force and resulting trauma teeth during normal brushing. The dentin specimens were positioned in the brush simulator and a medium tooth brush (Oral B, Flat trim indicator) rested on each specimen with a load of 150 g. The brush moved back and forth (1 stroke) and 10,000 brushing cycles were applied on each specimen (ISO 11609:2010).

EXAMPLE 2

Characterization

Atomic Force Microscopy (AFM):

Atomic Force Microscope (SPM-9500J3, Shimadzu Corp. Japan) was used for the assessment of dentin surface roughness. It provided the three-dimensional surface topography without any sample preparation. The microscopy was designed to scan the sample with a probe, measuring the local properties such as height, magnetism, and friction. The specimens from each group were selected randomly for investigation of AFM after treatment. The surface morphology of dentin was observed. A representative sample was selected and micrographs at six different areas were taken using Atomic Force Microscope equipped with AFM software (SPM-Offline, Shimadzu Corp. Japan). Surface roughness average (Ra) of all the groups with standard and mean deviations was be analyzed by AFM.

Scanning Electron Microscope-Energy Dispersive X-Ray Detector (SEM-EDX):

The surface morphology of the sample was examined by using a Scanning Electron Microscope (TESCAN VEGA-3 LMU, Check Republic). Samples were gold coated in gold SPUTTER COATER (QUORUM). Images were taken in the magnification range from 1500× to 5000× and operated at an accelerated voltage of 10-20 kV. Also, energy dispersive X-ray analysis (EDX, OXFORD INSTRUMENTS, UK) was conducted for identification of the abrasive elements.

Fluoride Release Analysis:

The experimental protocol used in this study was modified from the one suggested by Pearce [Pearce, E. A laboratory evaluation of New Zealand fluoride toothpastes, The New Zealand dental journal 70(320) (1974) 98-108; and Cury et al. Available fluoride in toothpastes used by Brazilian children, Brazilian dental journal 21(5) (2010) 396-400, incorporated herein by reference]. The study was carried out in quadruplicates. About 100 mg toothpastes sample from each group was taken separately in conical plastic centrifuge tubes which was then homogenized in 10 mL deionized water. Then, 5 mL from this suspension from each tube was centrifuged at 6000 rpm for ten minutes to remove the insoluble fluoride bound to the filler particles. From the extracted elute, 2.5 mL was transferred to two centrifuge tubes. 2.5 mL of two mole hydrochloric acid was then added to each 2.5 mL elute/suspension which was then conditioned at 45° C. for one hour. After adding 5 mL of one mole sodium hydroxide and one mL TISAB III reagent, the samples were analyzed via Ion Selective Electrode (ISE) potentiometry (Hanna HI3222 pH/ISE meter and Fluoride electrode) which was pre-calibrated at two points (1 ppm and 10 ppm) using fluoride standard solutions.

EXAMPLE 3

Antimicrobial Analysis

Antimicrobial Susceptibility Test (AST):

The test microbial strains i.e. S. mutans (ATCC 25175) and L. casei (ATCC 393) were obtained from American Type Culture Collection (ATCC, Manassas, Va., USA). The dehydrated culture media was purchased from Oxoid™ (Basingstoke, Hampshire, England) and Merck Millipore (Darmstadt, Germany). The culture media were prepared according to the manufacturer instructions. For the preparation of broths; measured amounts of dehydrated culture media powder was mixed with measured volume of distilled water at required temperature until completely dissolved. Prepared solutions were dispensed into final containers after sterilization.

For preparation of agar plates, solutions were made according to manufacturer guidelines. Following sterilization, the freshly prepared solutions were allowed to cool in a water bath (Anjue, AJ-HHS4, China) at a temperature range of 45-50° C. The cooled solutions were then poured into standard 90 mm flat-bottomed petri dishes. In order to ensure a standard depth of 4 mm, 20 mL of solution was poured in each petri dish. The petri dishes were then left to solidify at room temperature for two hours. Following solidification, all plates were placed in the refrigerator at 4° C.

In the case of L. casei, chocolate blood agar (CBA) was used. It was prepared by heating the prepared blood agar solution to an elevated temperature of 80° C. The heated solution was then sterilized, cooled and poured into petri dishes for solidification. Prior to conducting the experiment, all the laboratory equipment were sterilized in an autoclave at a temperature of 121° C., pressure of 15 psi, for 15 min. Same sterilization protocol was followed for dentifrices and molten culture media solutions before dispensing them into final containers.

Preparation of Dentifrices:

Three dilutions of each dentifrice were made with distilled water in the ratio 1:1, 1:2 and 1:4 respectively. Dentifrice slurries were vortexed in an electric shaker (Heidolph REAX 2000) and introduced in labeled, plastic containers.

Agar Well-Diffusion Assay:

Direct colony suspension method was used, according to EUCAST guidelines, for the preparation of inoculums. It involved preparing saline suspensions of isolated colonies, selected from overnight growth culture plates. Three to five well-isolated, similar colonies were selected and transferred to tubes containing 5 mL of 0.9% normal saline. The tubes were vortexed (Heidolph REAX 2000). To standardize the inoculum preparations for susceptibility testing, the suspensions were adjusted to a density equivalent to 0.5 Standard of the McFarland Turbidity Scale. This was done by visual comparison to McFarland turbidity standards kit and by using a photometric device (DensiCHEK plus, bioMérieux Inc., N.C., USA). Visual comparison was carried out against a white background. In this way, adjusted inoculum of both the bacterial strains S.mutans ATCC 25175 and L. casei ATCC 393 were prepared.

Inoculation of the Agar Plates:

Within fifteen minutes of the preparation of the adjusted inoculum suspensions, a sterile cotton swab was dipped in the respective tubes. The excess fluid was removed by pressing the swab against the wall of the tube. The inoculum was spread evenly over the entire surface of the respective agar plates of prepared media to create a bacterial lawn. The plates were rotated thrice at an angle of 60°, so that swabbing was accomplished evenly in three directions.

Measurement of Zones of Inhibition:

Following incubation, the resultant zones of inhibition were observed on the agar plates. These appeared as clear, circular halos surrounding the wells. The assessment of anti-cariogenic potential was done by recording the diameters of ZOI (mm). As the test was conducted in triplicate; mean values were calculated for each.

EXAMPLE 3

Determination of Roughness Caused by the Experimental Toothpastes

Atomic Force Microscopy (AFM):

Surface roughness was assessed using 3D-Atomic Force Microscope (SPM-9500J3, Shimadzu Corp, Japan) operating in non-contact mode. The roughness average (Ra) is the most widely used one dimensional (1D) roughness parameter, and denotes the arithmetic mean of the absolute values of the collected roughness data points. The surface of all groups showed signs of abrasion even when the brush was used with distilled water. Typical 3D images of abraded (after toothbrush simulation) and non-abraded dentin (polished surface) is illustrated in FIG. 1. 3D-images were reported in area selection of 10.0×10.0 μm.

The untreated portion (polished surface) presented relatively low values of surface roughness. However, as expected toothbrush abrasion caused visible nanoscale alterations on the surface of all samples to varying extent dependent on the toothpaste employed as illustrated by AFM 3D-images. The negative control group (distilled water) showed the least surface roughness, whereas the EXT-C group showed the highest surface roughness. The EXT-A & B groups showed slightly more surface roughness when compared to positive control group (Colgate cavity protection slurry), whereas EXT-D group (without abrasives) produced lesser surface roughness than positive control group.

Surface Roughness Average (Ra) Analysis by AFM

The results for the surface roughness average (Ra) with means and standard deviation of all groups are summarized in Table 2.

TABLE 3

Descriptive Analysis and Normality test of Ra

| Group | Mean (nm) | Standard Deviation | Kolmogorov Smirnov Sig | Remarks |
| --- | --- | --- | --- | --- |
| Distilled (Negative Control) | 9.0833 | 1.03425 | 0.981 | Normal |
| CT | 26.8167 | 1.05341 | 0.875 | Normal |
| EXT-A | 28.3667 | 1.77388 | 0.577 | Normal |
| EXT-B | 32.2833 | 1.47705 | 0.906 | Normal |
| EXT-C | 44.5333 | 3.93277 | 1 | Normal |
| EXT-D | 20.7667 | 1.15873 | 0.999 | Normal |

ANOVA test for the results in Table 3 was highly significant with p-value=0.000 and show that the results of the six experiments were significantly different in mean Ra. Kolmogorov Smirnov test indicated that the results of the six experiments followed normal distribution as such data are suitable to apply one way ANOVA. Leven's test of homogeneity of variance was significant with p-value=0.021. It indicated that variances of Ra of the above six experiments were not homogeneous. For one-to-one comparison, multiple comparison tests were performed by Tukey's and Tamhane's tests. Since Tukey's test is not advised in case variances of groups are not homogenous, Tamhane's test was also performed which is more robust in case of non-homogenous variances. The findings from both tests were quite similar. As per Tukey's results all experiments were significantly different from each other with p-value<0.05 except Colgate (Positive Control group) and Experimental paste A, there was no significant difference between the Colgate positive control and EXT-A with p-value=0.764.

The findings from Tamhane's test were quite similar that all groups were significantly different from each other with p-value<0.05 except Colgate (Positive Control group) and Experimental paste A, there was no significant difference between these two groups with p-value=0.802.

Relative Dentin Abrasivity (RDA) Calculation of the Experimental Pastes

EXT-A
According to the ISO 11609:2010(E)

$$RDA_{test} = \frac{Ra_{test} \times RDA_{ref}}{Ra_{ref}}$$

Where $RDA_{ref}$ is 70 (known value), $Ra_{test}$ is 28.3667 (measured value), and $Ra_{ref}$ is 26.8167 (measured value).

The resulting value of $RDA_{test}$ is 74.04.

EXT-B
According to the ISO 11609:2010(E)

$$RDA_{test} = \frac{Ra_{test} \times RDA_{ref}}{Ra_{ref}}$$

Where $RDA_{ref}$ is 70 (known value), $Ra_{test}$ is 32.2833 (measured value), and $Ra_{ref}$ is 26.8167 (measured value).

The resulting value of $RDA_{test}$ is 84.26

EXT-C
According to the ISO 11609:2010(E).

$$RDA_{test} = \frac{Ra_{test} \times RDA_{ref}}{Ra_{ref}}$$

Where $RDA_{ref}$ is 70 (known value), $Ra_{test}$ is 44.5333 (measured value), and $Ra_{ref}$ is 26.8167 (measured value).

The resulting value of $RDA_{test}$ is 116.24.

EXT-D
According to the ISO 11609:2010(E)

$$RDA_{test} = \frac{Ra_{test} \times RDA_{ref}}{Ra_{ref}}$$

Where $RDA_{ref}$ is 70 (known value), $Ra_{test}$ is 20.7667 (measured value), and $Ra_{ref}$ is 26.8167 (measured value).

The resulting value of $RDA_{test}$ is 54.20.

EXAMPLE 4

SEM Analysis of Morphology

Figure 2:
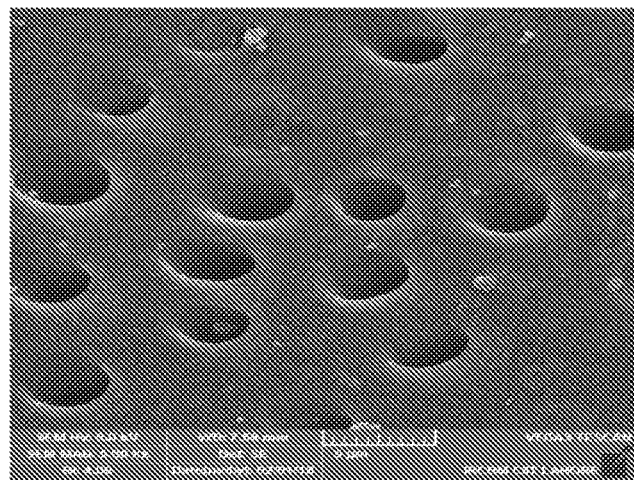
FIG. 2 shows an SEM micrograph of dentin surface morphology etched with 37% phosphoric acid showing open or patent dentinal tubules at ×5000 magnification.
Figure 3A:
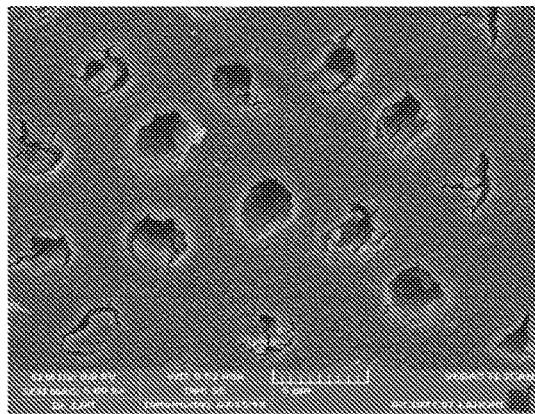
FIG. 3A shows an SEM micrograph of dentin at magnifications×5000 after rinsing with deionized water and sonication, negative control or distilled water.
Figure 3B:
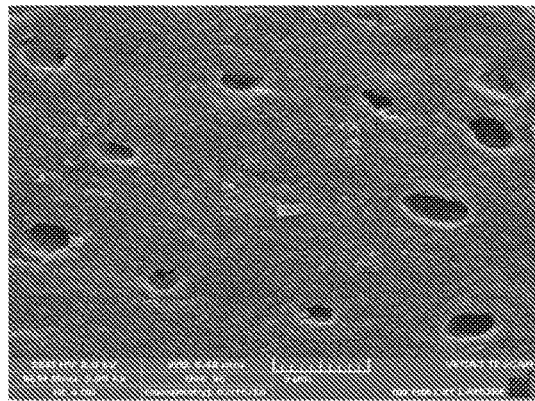
FIG. 3B shows an SEM micrograph at a magnification of ×5000 after rinsing with deionized water and sonication, positive control.
Figure 3C:
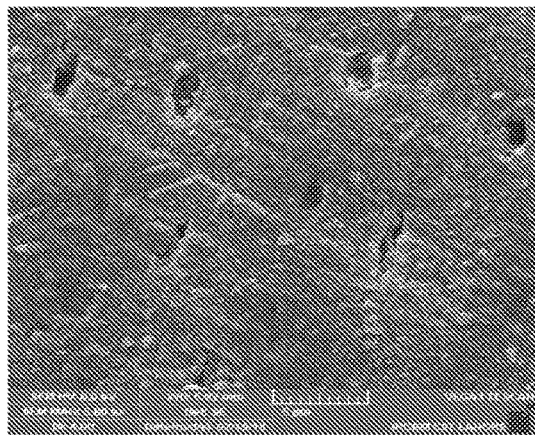
FIG. 3C shows an SEM micrograph of dentine treated with experimental paste A at a magnification of ×5000 after rinsing with deionized water and sonicating, negative control or distilled water.
Figure 3D:
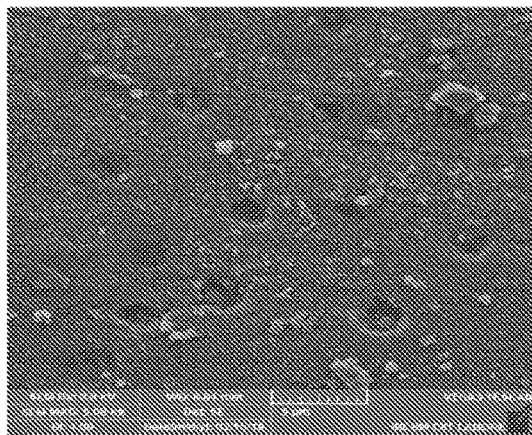
FIG. 3D shows an SEM micrograph of dentine treated with experimental paste B at a magnification of ×5000 after rinsing with deionized water and sonication, negative control or distilled water.
Figure 3E:
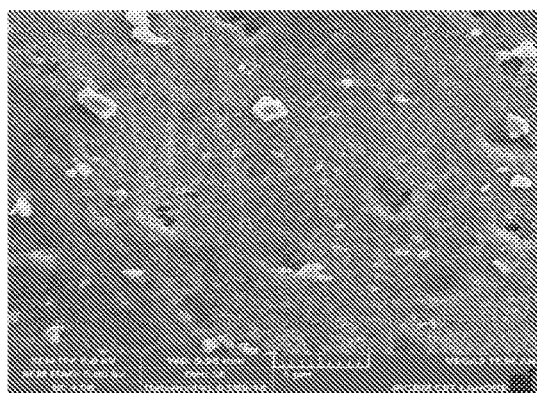
FIG. 3E shows an SEM micrograph of dentine treated with experimental paste C at a magnification of ×5000 after rinsing with deionized water and sonication, negative control or distilled water.
Figure 3F:
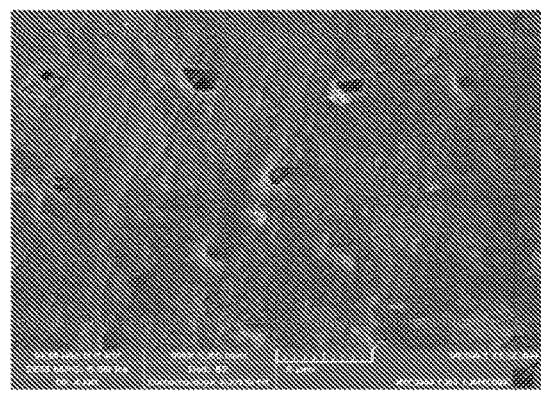
FIG. 3F shows an SEM micrograph of dentine treated with experimental paste D at a magnification of ×5000 after rinsing with deionized water and sonication, negative control or distilled water.

SEM analysis was performed to assess the surface morphology. Surface morphology of the etched dentin is given in FIG. 2 showing open or patent dentinal tubules. FIGS. 3A-3F show SEM micrographs for simulated brushing with distilled water (negative control), Colgate cavity protection slurry (positive control), and experimental pastes A, B, C and D slurries for samples rinsed with deionized water followed by sonication for 10 sec.

SEM micrographs of etched dentin with 37% phosphoric acid for 30 sec showed open or patent dentinal tubules. Control samples which were rinsed with deionized water followed by sonication for 10 sec, and brushing with distilled water showed smooth dentin surface with open or patent dentinal tubules and some particles on dentin surface. Also, positive control samples brushed with Colgate cavity protection slurry showed relatively smooth dentin surface with open or patent dentinal tubules and few particles on the dentin surface and some were partially obliterated. SEM micrographs of samples brushed with experimental paste A slurry showed a smear layer like coating covering all the dentin surface and uniform occlusion of almost all the dentinal tubules. Very few tubule orifices remained partially opened with maximum narrowing of tubular lumen. Also experimental paste B slurry produced a smear layer like coating covering the entire dentin surface that completely occluded almost all the dentinal tubules. Micrographs of experimental paste slurry C showed similar results with uniform occlusion of almost all the dentinal tubules by a smear layer like coating and only a few tubule orifices showed partial obliteration with maximum narrowing of the tubular lumen. Experimental paste slurry D showed relatively smooth surface with open dentinal tubules with the presence of few particles on dentin surface and some were partial obliterated.

The result in FIG. 2 clearly shows that the untreated itched tooth shows tubules having dimeters in the range of about 1 to 5 μm. Upon treatment with the experimental compositions A-D the tubules occluded at least by 40%, at least 50%, at least 60%, at least 70%, at least 80%, at least 90%, and even some were completely occluded with some having an opening in the range of less than 1 to 2 μm, compare FIGS. 3A to 3E and 3F.

Elemental Analysis by SEM-EDX

EDX analysis commenced on the etched dentin surface showed large amounts of carbon and oxygen. Calcium, phosphate and sodium were rarely observed. The most common elements detected in samples brushed with distilled water were carbon and oxygen. Colgate cavity protection treatment showed large amounts of carbon and oxygen while only trace amounts of calcium, silicon and sodium. However in samples treated with experimental pastes A, B and C calcium and phosphate became the dominant elements including the presence of silicon, sodium, fluoride and zinc while experimental paste D without abrasives showed high amounts of carbon and oxygen with only trace amounts of calcium, phosphate, sodium and silicon. Particle size analysis of samples treated with experimental pastes A, B and C showed attachment of nano-sized fluoride containing bioactive particles and nano-oxides occluding almost all the dentinal tubules and maximum narrowing of tubular lumen in few remaining tubules (remineralization) at magnifications of ×10000 and EDX confirmed the attachment of dentin like structure.

EXAMPLE 5

Fluoride Release Analysis

Both elutes and suspensions of the commercial toothpaste showed fluoride release of 6.55 ppm in elutes and 6.28 ppm in suspensions. Maximum mean fluoride release (FR) exhibited by suspensions of the experimental toothpastes in descending order was as follows: EXT-C (14.16 ppm), EXT-B (11 ppm), and EXT-A (3.52 ppm). Maximum mean FR exhibited by elutes of the experimental toothpastes given in descending order was as follows: EXT-B (10.79 ppm), EXT-C (9.95 ppm), and EXT-A (9.64 ppm).

EXAMPLE 6

Antimicrobial Analysis
Antimicrobial Susceptibility Test (AST)

Characteristic zones of inhibition were visible for the experimental and commercial dentifrices, when tested against the microbial strains *S. mutans* and *L. casei*, under different conditions. Zones of inhibition against *S. mutans* appeared after 24 h; whereas in the case of *L. casei*, the zones were visible after 48 h. Mean values (n=3) and standard deviations of diameters of zones of inhibition (mm) recorded for experimental and commercial dentifrices against *S. mutans* are *L. casei* are summarized in Table 3 and 4 respectively. CT was found to have the highest inhibition zone against both microbial strains, at all dilutions, however the difference was insignificant.

TABLE 3

Zone of inhibition shown by various toothpastes with *Lactobacillus casei*

| | Measurement of Zones of inhibition (mm) | | | | | |
|---|---|---|---|---|---|---|
| | Dilution 1:1 | | Dilution 1:2 | | Dilution 1:4 | |
| Dentifrice | Mean | SD | Mean | SD | Mean | SD |
| EXT-A | 20.5 | 0.408 | 18.17 | 0.623 | 17 | 0.816 |
| EXT-B | 25.33 | 0.471 | 22.33 | 0.943 | 20.17 | 0.624 |
| EXT-C | 26.1 | 0.535 | 23.17 | 1.027 | 21.67 | 0.471 |
| CT | 26.33 | 0.942 | 23.06 | 1.715 | 21 | 1.632 |

TABLE 4

Zone of inhibition shown by various toothpastes with *S. mutans*

| | Measurement of Zones of inhibition (mm) | | | | | |
|---|---|---|---|---|---|---|
| | Dilution 1:1 (1 g/ml) | | Dilution 1:2 (1 g/2 ml) | | Dilution 1:4 (1 g/4 ml) | |
| Dentifrice | Mean | SD | Mean | SD | Mean | SD |
| EXT-A | 21.17 | 1.027 | 16.5 | 0.408 | 15.83 | 0.236 |
| EXT-B | 23.67 | 0.471 | 19 | 0.816 | 16.67 | 0.943 |
| EXT-C | 25.33 | 0.849 | 21 | 0.816 | 18.83 | 0.624 |
| CT | 26 | 1.632 | 23 | 0.816 | 19.83 | 0.236 |

The invention claimed is:

1. A method of controlling dental caries and treating teeth sensitivity, comprising:

applying a toothpaste composition to teeth, and
brushing the teeth for a time of at least one minute;
wherein the toothpaste composition comprises:
(a) *Nigella sativa* oil in an amount of 3 wt. %;
(b) an amount of water in the range of 33 wt. % to 36 wt. %;
(c) sodium lauryl sulfate in the range of 1 wt. % to 2 wt. %,
(d) glycerol in the range of 29 wt. % to 32 wt. %,
(e) sodium benzoate in the range of 0.5% to 1.0 wt. %,
(f) methyl cellulose in the range of 0.5% to 1.0 wt. %,
(g) calcium carbonate in the range of 24 wt. % to 27 wt. %,
(h) flavoring agent in the range of 0.5% to 1.0 wt. %,
(i) fluoride-doped bioactive glass in an amount of 1.5 wt. %;
(j) zinc oxide in an amount of 3.0 wt. %; and
(k) titanium oxide in an amount of 2 wt. %;
wherein the wt. % is present by weight of the total weight of the toothpaste and the toothpaste composition has a maximum mean bioglass fluoride release in elutes of 9.95 to 10.75 ppm.

2. The method of claim 1, wherein the toothpaste comprises water in an amount of about 36 wt. % of the total weight of the toothpaste.

3. The method of claim 1, wherein the sodium lauryl sulfate is present in an amount of 2 wt. % of the total weight of the toothpaste.

4. The method of claim 1, wherein the sodium benzoate is present in an amount of about 1 wt. % of the total weight of the toothpaste.

5. The method of claim 1, wherein the flavoring agent is present in an amount of about 1 wt. % of the total weight of the toothpaste.

* * * * *